US008864688B2

(12) United States Patent
Azzolini

(10) Patent No.: US 8,864,688 B2
(45) Date of Patent: Oct. 21, 2014

(54) PROBE FOR ENTERAL NUTRITION
(76) Inventor: Graziano Azzolini, Cavezzo (IT)
( * ) Notice: Subject to any disclaimer, the term of this patent is extended or adjusted under 35 U.S.C. 154(b) by 309 days.
(21) Appl. No.: 13/203,046
(22) PCT Filed: Feb. 10, 2010
(86) PCT No.: PCT/IB2010/000248
§ 371 (c)(1), (2), (4) Date: Sep. 8, 2011
(87) PCT Pub. No.: WO2010/097666
PCT Pub. Date: Feb. 9, 2010
(65) Prior Publication Data
US 2012/0123300 A1 May 17, 2012
(30) Foreign Application Priority Data
Feb. 24, 2009 (IT) .............................. MO2009A0047
(51) Int. Cl.
| A61B 5/103 | (2006.01) |
| A61J 15/00 | (2006.01) |
| A61M 25/00 | (2006.01) |
| A61B 5/00 | (2006.01) |
| A61B 5/03 | (2006.01) |
| A61M 25/10 | (2013.01) |
| A61B 6/12 | (2006.01) |

(52) U.S. Cl.
CPC .......... *A61J 15/0049* (2013.01); *A61J 15/0003* (2013.01); *A61M 25/007* (2013.01); *A61M 2025/0003* (2013.01); *A61J 2015/0088* (2013.01); *A61J 2015/0084* (2013.01); *A61B 6/12* (2013.01); *A61B 5/4238* (2013.01); *A61B 5/037* (2013.01); *A61J 15/0073* (2013.01); *A61B 5/6853* (2013.01); *A61M 25/1011* (2013.01)
USPC ............................ 600/593; 600/561; 600/587

(58) Field of Classification Search
CPC .......... A61B 5/037; A61B 5/42; A61B 5/041
USPC .............................. 33/511, 512; 600/587, 593
See application file for complete search history.

(56) References Cited

U.S. PATENT DOCUMENTS 5,085,216 A * 2/1992 Henley et al. ................. 600/367
5,645,539 A * 7/1997 Solomon et al. .............. 604/533
(Continued)

FOREIGN PATENT DOCUMENTS

| EP | 1 695 684 A1 | 8/2006 |
| FR | 2 897 540 A1 | 8/2007 |

OTHER PUBLICATIONS

International Search Report, dated Jun. 21, 2010, from corresponding PCT application.

*Primary Examiner* — Sean Dougherty
*Assistant Examiner* — Daniel Cerioni
(74) *Attorney, Agent, or Firm* — Young & Thompson

(57) ABSTRACT

A probe (1) for enteral nutrition includes a tubular element (2) of elongated shape and flexible, with a first extremity (2a) having a supply mouth (4) for the introduction of nutritional substances or the like and a second extremity (2b) positionable inside the stomach of a patient and having at least a dispensing hole (6) for dispensing the nutritional substances, the tubular element (2) having a main channel (7) of communication between the supply mouth (4) and the dispensing hole (6). The probe (1) includes at least a first and a second reading element (8, 9) for reading the pressure inside the digestive system of the patient at two distinct sections of the tubular element (2).

19 Claims, 2 Drawing Sheets

(56) References Cited

U.S. PATENT DOCUMENTS

| | | |
|---|---|---|
| 5,718,685 A | 2/1998 | Roewer et al. |
| 6,283,719 B1 * | 9/2001 | Frantz et al. ............... 417/53 |
| 6,299,583 B1 * | 10/2001 | Eggers et al. ............. 600/526 |
| 6,322,518 B1 * | 11/2001 | Young et al. .............. 600/505 |
| 7,229,429 B2 * | 6/2007 | Martin et al. ................ 604/43 |
| 8,152,951 B2 * | 4/2012 | Zawacki et al. ............ 156/290 |
| 2003/0212381 A1 * | 11/2003 | Whitehead, III ........... 604/514 |
| 2004/0054350 A1 * | 3/2004 | Shaughnessy et al. ..... 604/535 |
| 2008/0167607 A1 * | 7/2008 | Pfeiffer et al. .......... 604/97.01 |
| 2008/0319391 A1 * | 12/2008 | Jackson ..................... 604/142 |
| 2009/0318757 A1 * | 12/2009 | Singh ......................... 600/109 |

\* cited by examiner

Fig. 2
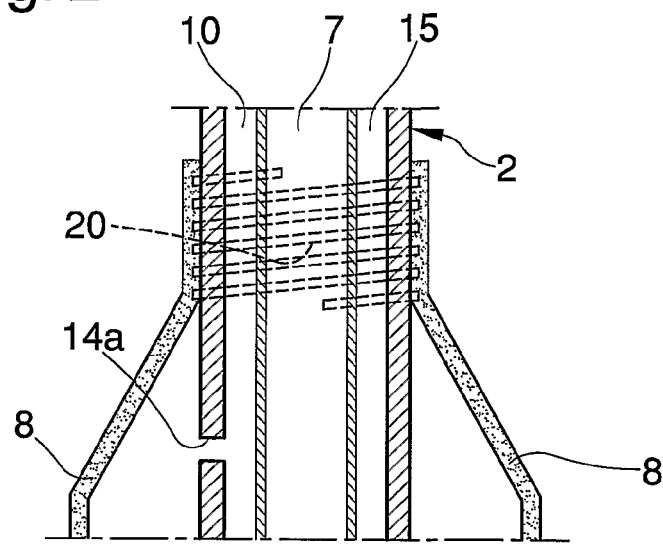
Fig. 3
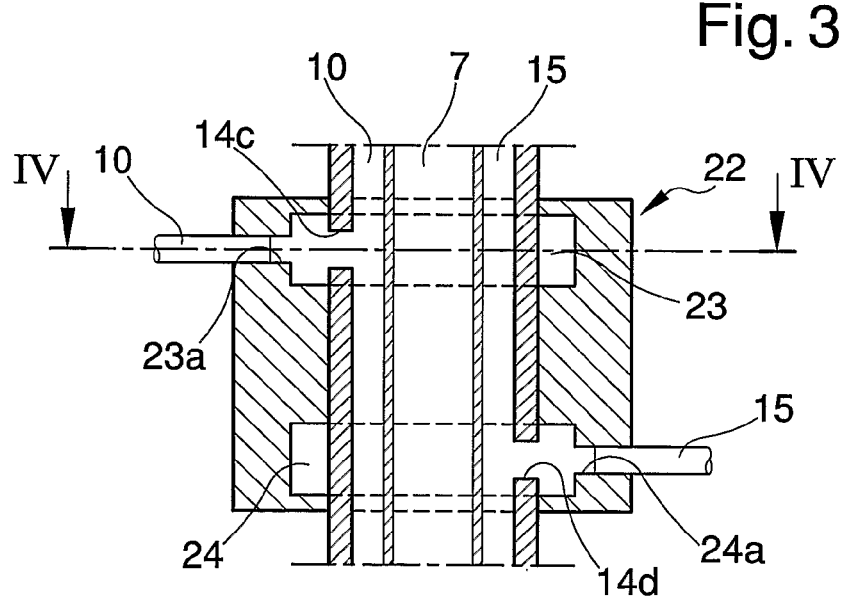
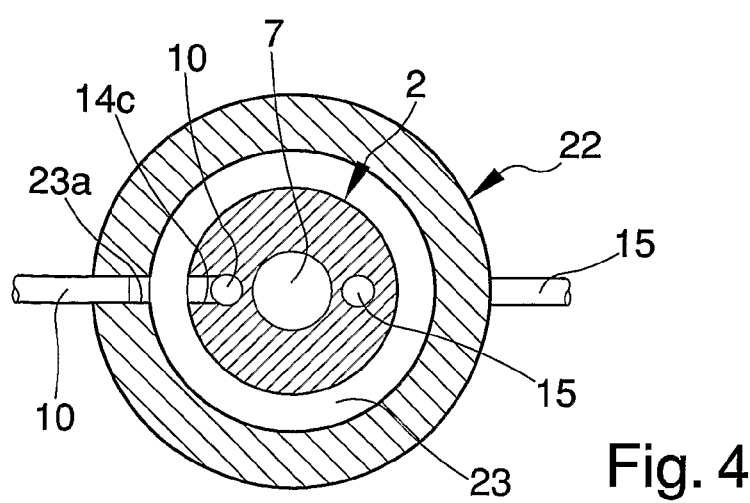
Fig. 4

PROBE FOR ENTERAL NUTRITION

TECHNICAL FIELD

The present invention relates to a probe for enteral nutrition.

BACKGROUND ART

In the medical field, the so-called enteral nutrition is known of patients who necessarily have to be artificially fed.

In medical practice, to perform such nutrition, gastric probes of various types are used, classified by site of location and type of use.

Nasogastric probes, e.g., are suitable for being introduced into a nostril of the nose, through the throat and the oesophagus as far as the patient's stomach.

The known probes generally comprise a tubular element, made of soft and flexible material, of the silicone or polyurethane type, with section and length that varies according to the type of application and age of the patient.

The distal extremity of the tubular element can be positioned inside the stomach of a patient and is commonly provided with a plurality of holes for dispensing the nutritional substances.

The proximal extremity of the tubular element is provided with a mouth for supplying the nutritional substances, which can be administered both by gravity and by means of suitable positive-displacement pumps.

Also known is the enteral nutrition of artificially-ventilated patients, e.g., in the case of the patient's normal vital functions being jeopardised or altered following an acute illness or traumatic event.

Consequently, it is necessary to read the pressure at several points along the small probe in order to adequately regulate the assisted ventilation of the patient.

To cater for this need, probes for enteral nutrition are known having a balloon made of elastic material which is arranged at a section of the tubular element and which is connected to a suitable transducer able to determine the pressure present outside the balloon itself.

These known probes do however have a number of drawbacks.

In particular, the known probes allow reading the pressure at only one point along the tubular element, thereby considerably restricting the quality of patient monitoring and, therefore, the possibility of adequately intervening to regulate the assisted ventilation.

Object of the Invention

The main aim of the present invention is to provide a probe for enteral nutrition which allows performing accurate monitoring of the patient's pressure parameters, e.g., by reading the oesophagus pressure and the gastric pressure, so as to allow adequately intervening to regulate the assisted ventilation of the patient.

Another object of the present invention is to provide a probe for enteral nutrition which allows to overcome the mentioned drawbacks of the known art in the ambit of a simple, rational, easy, effective to use and low cost solution.

The above objects are achieved by the present probe for enteral nutrition, comprising at least a tubular element of elongated shape, with a first extremity having at least a supply mouth for the introduction of nutritional substances or the like and a second extremity positionable inside the stomach of a patient and having at least a dispensing hole for dispensing said nutritional substances, said tubular element having at least a main channel of communication between said supply mouth and said dispensing hole, characterized by the fact that it comprises at least a first and a second reading element for reading the pressure inside the digestive system of the patient at two distinct sections of said tubular element.

BRIEF DESCRIPTION OF THE DRAWINGS

Other characteristics and advantages of the present invention will become more evident from the description of a preferred, but not sole, embodiment of a probe for enteral nutrition, illustrated purely as an example but not limited to the annexed drawings in which:

FIG. 2 is a side and section view of a detail of the probe according to the invention of FIG. 1;

FIG. 3 is a side and section view of a detail of the probe according to the invention of FIG. 1;

FIG. 4 is a section view along the section plane IV-IV of the probe according to the invention of FIG. 3.

EMBODIMENTS OF THE INVENTION

Figure 1:
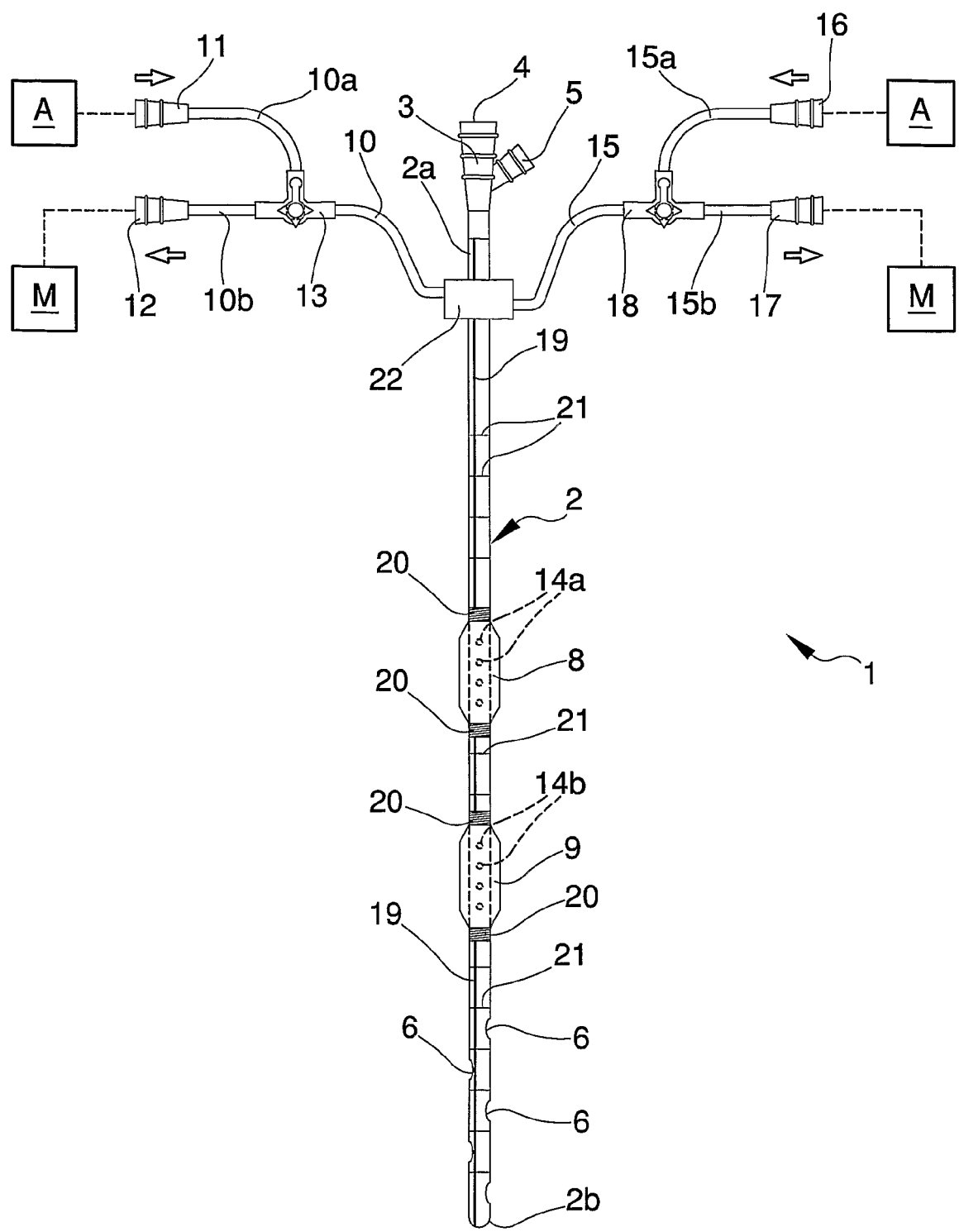
FIG. 1 is a side schematic view of the probe for enteral nutrition according to the invention.

With particular reference to such figures, globally by 1 has been indicated a probe usable in the medical field to perform the so-called enteral nutrition of patients who necessarily have to be artificially fed.

The probe 1 comprises a tubular element 2 of elongated shape which is made of elastic and flexible material, of the PVC, polyurethane type or the like, and which can be inserted, at least in part, through the oesophagus as far as the stomach of a patient.

In particular, in the case of the probe 1 being of the nasogastric type, the tubular element 2 can be introduced into a nostril of the nose, through the throat and the oesophagus as far as the patient's stomach. The manufacture of a probe 1 of different type cannot however be ruled out and, consequently, the length and the diameter of the cross section of the tubular element 2 will vary according to the site of application and age of the patient.

The tubular element 2 has a first proximal extremity 2a to which is fixed a first connector 3 having a supply mouth 4 for the introduction of nutritional substances to be administered to a patient.

The first connector 3, in particular, can be associated with a suitable positive-displacement pump or, alternatively, with a bag containing the nutritional substances. In this latter case, the nutritional substances are administered by gravity through the supply mouth 4.

Usefully, the first connector 3 can be provided with a supplementary mouth 5 usable for the extemporaneous administration of substances such as pharmaceuticals, etc., or to unblock the probe 1.

The tubular element 2, furthermore, has a second distal extremity 2b, closed and formed like a semi-sphere to limit any injuries for the patient, which can be positioned inside the stomach of a patient and which has a plurality of dispensing holes 6 distributed on the side and suitable for dispensing the nutritional substances.

A main channel 7 suitable for being crossed by the nutritional substances extends from the first extremity 2a to the second extremity 2b, inside the tubular element 2, and connects the supply mouth 4 to the dispensing holes 6.

The main channel 7 is entirely made inside the tubular element 2 and in a single body with it.

Advantageously, the probe 1 comprises a first and a second pressure reading element, indicated in FIG. 1 by the numbers 8 and 9 respectively, suitable for reading the pressure inside the digestive system of a patient at two distinct sections of the tubular element 2.

In particular, the first reading element 8 and the second reading element 9 are composed of a first and a second balloon respectively, both made of elastic and soft polymer material, suitable for detecting small changes in pressure.

Usefully, the first balloon 8 can be suitably arranged at the patient's oesophagus so as to read the oesophagus pressure, while the second balloon 9 can be suitably arranged inside the patient's stomach so as to read the gastric pressure.

A different arrangement of the first and of the second balloons 8 and 9 cannot however be ruled out, nor can the use of a different type and of a different number of reading elements.

During use, the first and the second balloons 8 and 9 can be connected to one or more monitoring units M having a transducer device of the pressures read outside the balloons and means for displaying such pressure values.

Usefully, this monitoring unit M can be accessible to a medical operator charged with the assisted ventilation of a patient, who can regulate the parameters of this assisted ventilation according to the read pressure values.

Consequently, the monitoring of the pressure at several points along the tubular element 2 of the probe 1 allows a more precise measurement of the patient's pressure values and, consequently, allows performing a more accurate and effective regulation of assisted ventilation.

Advantageously, the probe 1 comprises a first auxiliary channel 10 suitable for being crossed by a fluid, preferably air, which extends inside the tubular element 2 as far as the first balloon 8 and which connects the first balloon itself to the monitoring unit M.

In particular, the first auxiliary channel 10 comprises a portion outside the tubular element 2, comprising a first branch 10a and a second branch 10b having a second connector 11 and a third connector 12 associable, respectively, with an air supply unit A for supplying air to the first balloon 8 and to the above monitoring unit M.

A connection element 13 between the first branch 10a and the second branch 10b, composed of a tap that can be operated manually or of a similar device allows connecting, alternatively, the first balloon 8 to the monitoring unit M or to the supply unit A.

The first balloon 8 is substantially elongated and has, at the extremities, two openings substantially opposite one another, inside which is inserted watertight a section of the tubular element 2.

As shown in FIG. 2, at the first balloon 8 the tubular element 2 has one or more communication holes 14a with the first auxiliary channel 10.

Similarly, the probe 1 comprises a second auxiliary channel 15 suitable for being crossed by a fluid, preferably air, which extends inside the tubular element 2 as far as the second balloon 9 and which connects the second balloon itself to a monitoring unit M.

In particular, the second auxiliary channel 15 comprises a portion outside the tubular element 2, comprising a first branch 15a and a second branch 15b having a second connector 16 and a third connector 17 associable, respectively, with an air supply unit A for supplying air to the second balloon 9 and to the above monitoring unit M.

A connection element 18 between the first branch 15a and the second branch 15b, composed of a tap that can be operated manually or by a similar device, allows connecting alternatively the second balloon 9 to the monitoring unit M or to the supply unit A.

The second balloon 9 is substantially elongated and has, at the extremities, two openings substantially opposite one another, inside which is inserted watertight a section of the tubular element 2.

At the second balloon 9, the tubular element has one or more communication holes 14b with the second auxiliary channel 15.

Usefully, the cross section of the main channel 7, which is suitable for being crossed by the nutritional substances, is of considerably bigger dimensions than the dimensions of the cross sections of the first and of the second auxiliary channels 10 and 15.

Furthermore, the first and the second auxiliary channels 10 and 15 can be positioned differently inside the tubular element 2 and the presence of further auxiliary channels cannot be ruled out.

Advantageously, the outer portions of the first and of the second auxiliary channels 10 and 15 are connected to the respective inner portions of the tubular element 2 by means of a connection element, indicated in FIG. 1 by reference numeral 22 and illustrated in detail in FIGS. 3 and 4.

Particularly, the connection element 22 has a tubular shape and is fitted to measure and watertight on the tubular element 2, at a section in which the tubular element itself has a communication hole 14c with the first auxiliary channel 10 and a communication hole 14d with the second auxiliary channel 15.

Usefully, the connection element 22 has a first annular chamber 23 positionable at the hole 14c and a second annular chamber 24 positionable at the hole 14d.

The first and the second chambers 23 and 24 are then provided with a first opening 23a and with a second opening 24a, respectively, communicating with the outside, in which can be fitted to measure and watertight the free extremities, respectively, of the outer portion of the first auxiliary channel 10 and of the outer portion of the second auxiliary channel 15.

The particular annular shape of the first and the second chambers 23 and 24 make it easy to position the connection element 22 on the tubular element 2, considerably simplifying the operations of alignment with the openings 23a and 24a on the tubular element itself.

The presence of the connection element 22, furthermore, permits an easy connection between the outer portions and inner portions of the first and second auxiliary channels 10 and 15, making any replacements, e.g., easier.

Usefully, the tubular element 2 is made of substantially transparent material and comprises marker means for marking the position of the probe 1, made of radiopaque material, displayable by means of radiography.

In point of fact, the presence of such marker means allows displaying, by means of radiography and during and after fitting, the position of the tubular element 2 inside the patient's oesophagus and stomach, thus favouring the correct positioning thereof.

In particular, the marker means comprise a trace 19 in radiopaque material that extends longitudinally along the entire tubular element 2.

The marker means also comprise wrappings 20 in radiopaque material, made using tungsten filaments or the like, wrapped around respective sections of the tubular element 2, near the openings of the first and second balloons 8 and 9.

Such wrappings are required to display the position of the first and second balloons 8 and 9 inside the patient's organs.

Usefully, the wrappings 20 are made in a single body with the first and the second balloons 8 and 9, at the respective extremities having the openings, so as not to jeopardize the perfect watertight seal of the first and the second balloons 8 and 9 with respect to the tubular element 2 and so as to prevent any injuries to the patient that could occur in case of the accidental removal of one of the wrappings 20 from the probe 1.

Usefully, along its outer surface, the tubular element has a sequence of notches 21 which make up a graduated scale usable by a medical operator to allow the correct positioning of the probe 1 inside the digestive system of a patient.

During use, the tubular element 2 of the probe 1 is fitted by a medical operator inside the oesophagus as far as the patient's stomach, e.g., through the nose.

Such fitting can be done, e.g., so as to suitably position the first and the second balloons 8 and 9 for reading, respectively, the oesophagus pressure and the gastric pressure.

Subsequently, the first connector 3 is connected to the supply line of the nutritional substances, while the second connectors 11 and 16 and the third connectors 12 and 17 at the proximal extremities of the first and the second auxiliary channels 10 and 15 are connected, respectively, to one or more supply units A and to one or more monitoring units M.

The taps 13 and 18 are then suitably positioned so as to allow the connection between the first and the second balloons 8 and 9 and the supply unit A.

The first and the second balloons 8 and 9 are then inflated until they reach a predefined pressure by means of the introduction of air by the supply unit A and through the first and the second auxiliary channels 10 and 15.

The taps 13 and 18 are then suitably positioned so as to allow the connection between the first and the second balloons 8 and 9 and the monitoring unit M.

In such a way, the values and variations in pressures outside the first and second balloons 8 and 9 are conveyed by means of the first and the second auxiliary channels 10 and 15 to the monitoring unit M.

An appointed medical operator can then check these pressure values, by consulting the monitoring unit M and then consequently change the patient's assisted-ventilation parameters.

It has in practice been found how the invention described achieves the intended objects.

In particular, it is underlined that the probe for enteral nutrition according to the invention permits effecting the transfer of the nutritional substances to a patient and, at the same time, an accurate monitoring of the pressure parameters of the patient him/herself, e.g., by reading the oesophagus pressure and the gastric pressure, so as to allow adequate interventions to regulate the assisted ventilation.

The invention claimed is:

1. A probe for enteral nutrition, comprising:
    at least one tubular element of elongated shape and substantially flexible, with a first extremity having at least one supply mouth for an introduction of nutritional substances and a second extremity positionable inside the stomach of a patient and having at least a dispensing hole configured to dispense the nutritional substances, the tubular element having at least one main communication channel between the supply mouth and the dispensing hole;
    at least a first reading element and a second reading element respectively configured to read pressure inside the digestive system of the patient at two distinct sections of the tubular element;
    at least one first auxiliary channel of communication between the first reading element and a monitoring unit configured to monitor the read pressure;
    at least one second auxiliary channel of communication between the second reading element and the monitoring unit; and
    at least one first connection element between the tubular element and outer portions of the first and second auxiliary channels disposed outside of the tubular element, the first connection element having a tubular shape and being fit watertightly on the tubular element at a section in which the tubular element has a first communication hole communicating with an inner portion of the first auxiliary channel, the inner portion of the first auxiliary channel being disposed inside the tubular element, and in which the tubular element has a second communication hole communicating with an inner portion of the second auxiliary channel, the inner portion of the second auxiliary channel being disposed inside the tubular element,
    the first connection element comprising
        a first annular chamber positionable at the first communication hole, and
        a second annular chamber positionable at the second communication hole,
        the first annular chamber being provided with a first opening associable with at least one extremity of the outer portion of the first auxiliary channel, and the second annular chamber being provided with a second opening associable with at least one extremity of the outer portion of the second auxiliary channel.

2. The probe according to claim 1, wherein at least one of the first reading element and the second reading element is associated with the monitoring unit configured to monitor the read pressure.

3. The probe according to claim 1, wherein the main channel, the first auxiliary channel, and the second auxiliary channel are at least partially inside the tubular element.

4. The probe according to claim 1, wherein at least one of the first reading element and the second reading element comprises at least one balloon of elastic material.

5. The probe according to claim 4, wherein the balloon is associable with at least one supply unit to supply a fluid.

6. The probe according to claim 5, wherein at least one of the first auxiliary channel and the second auxiliary channel is associable with the supply unit.

7. The probe according to claim 6, wherein at least one of the first auxiliary channel and the second auxiliary channel comprises at least one second connection element for an alternative connection to the monitoring unit or to the supply unit.

8. The probe according to claim 7, wherein the second connection element is a manually-operated tap.

9. The probe according to claim 5, wherein the balloon comprises at least two openings substantially opposite one another, a section of the tubular element being fitted watertightly inside the balloon by passing through the two opposite openings.

10. The probe according to claim 5, wherein, at the balloon, the tubular element has at least one third communication hole, the third communication hole being configured to communicate with the first auxiliary channel or the second auxiliary channel.

11. The probe according to claim 4, further comprising marking means for marking the position of the probe, the marking means being made of radiopaque material and displayable by radiography.

12. The probe according to claim 11, wherein the marking means comprises at least one trace of radiopaque material that extends longitudinally along at least one section of the tubular element.

13. The probe according to claim 11, wherein the marking means comprises at least one wrapping of radiopaque material arranged in the proximity of an extremity of balloon.

14. The probe according to claim 13, wherein the wrapping and the balloon form a single body.

15. The probe according to claim 7, further comprising a first connector associated with the first extremity and having the supply mouth.

16. The probe according to claim 15, wherein at least one of the first reading element and the second reading element comprises at least one balloon of elastic material, the balloon being associable with at least one supply unit to supply a fluid,
at least one of the first auxiliary channel and the second auxiliary channel is associable with the supply unit,
at least one of the first auxiliary channel and the second auxiliary channel comprises the first connection element for an alternative connection to the monitoring unit or to the supply unit, and
at least one of the first auxiliary channel and the second auxiliary channel comprises a second connector and a third connector, the second connector being arranged upstream with respect to the second connection element and associable with the supply unit, the third connector being arranged upstream of the second connection element and associable with the monitoring unit.

17. The probe according to claim 1, wherein the first reading element is configured to read the oesophagal pressure of the patient.

18. The probe according to claim 1, wherein the second reading element is configured to read the gastric pressure of the patient.

19. The probe according to claim 1, wherein the at least one first connection element connects the outer portion of the first auxiliary channel to the outer portion of the second auxiliary channel through the first communication hole and the inner portion of the first auxiliary channel and the second communication and the inner portion of the second auxiliary channel.

* * * * *